US006900721B1

United States Patent
Urbas et al.

(10) Patent No.: US 6,900,721 B1
(45) Date of Patent: May 31, 2005

(54) IMPLANTABLE INDUCTIVELY PROGRAMMED TEMPERATURE SENSING TRANSPONDER

(75) Inventors: Donald J. Urbas, Evergreen, CO (US); David Ellwood, Lake wood, CO (US); Eric B. Weddington, Evergreen, CO (US)

(73) Assignee: Bio Medic Data Systems, Inc., Seaford, DE (US)

( * ) Notice: Subject to any disclaimer, the term of this patent is extended or adjusted under 35 U.S.C. 154(b) by 0 days.

(21) Appl. No.: 09/502,696

(22) Filed: Feb. 11, 2000

(51) Int. Cl.[7] .............................. H04Q 5/22; G06F 12/00
(52) U.S. Cl. .............................. 340/10.51; 340/870.17; 711/1; 711/100; 711/144; 711/145
(58) Field of Search ........................... 340/10.51, 10.34, 340/870.17; 711/1, 100, 125, 144, 145, 156

(56) References Cited

U.S. PATENT DOCUMENTS

| 4,602,871 A | | 7/1986 | Hanaoka | |
|---|---|---|---|---|
| 4,648,055 A | | 3/1987 | Ishizaka et al. | |
| 5,479,172 A | | 12/1995 | Smith et al. | |
| 5,517,194 A | * | 5/1996 | Carroll et al. | ............ 340/10.34 |
| 5,701,121 A | * | 12/1997 | Murdoch | ................. 340/10.34 |
| 5,767,792 A | * | 6/1998 | Urbas et al. | ........... 340/870.17 |
| 5,945,920 A | | 8/1999 | Maletsky | |
| 5,978,192 A | * | 11/1999 | Young et al. | ................. 361/56 |

FOREIGN PATENT DOCUMENTS

| EP | 0 833 169 A1 | 4/1998 |
|---|---|---|
| GB | 2 297 225 A | 7/1996 |

* cited by examiner

Primary Examiner—Brian Zimmerman
Assistant Examiner—Clara Yang
(74) Attorney, Agent, or Firm—Stroock & Stroock & Lavan LLP

(57) ABSTRACT

A transponder includes a memory, the memory having a data region and a status byte region. A clock generator receives a program signal and outputs a data latch signal. An address module receives the address latch signal and addresses predetermined adresses in the memory. A program control reads the status byte from the memory and outputs a program enable signal in response thereto causing the clock generator to output the address latch in response to the program enable signal. The memory may further include a user lock region, where in the data stores characters therein and the user lock having a plurality of bits, each bit corresponding to a respective character. A lock status being stored in each bit of the user lock region to indicate whether the corresponding character may be reprogrammed.

19 Claims, 11 Drawing Sheets

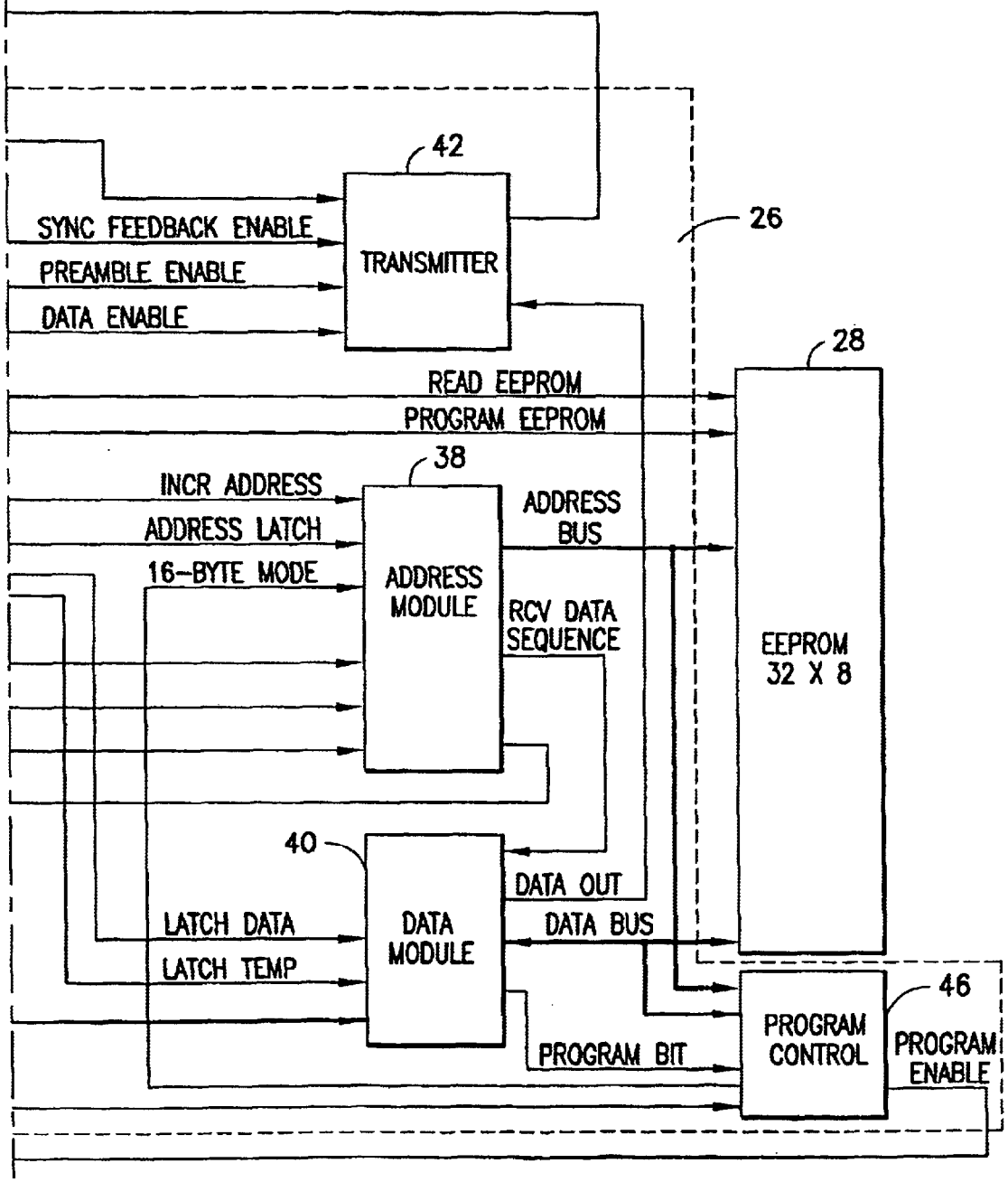

IMPLANTABLE INDUCTIVELY PROGRAMMED TEMPERATURE SENSING TRANSPONDER

BACKGROUND OF THE INVENTION

The present invention is directed to an implantable inductively programmable temperature sensing transponder, and, more particularly, to a transponder having operations which may be modified through software control Implantable programmable temperature transponders are passive devices that are implanted under the skin of laboratory animals, by way of example, for positive animal identification. As is known in the art, conventional transponders, such as those sold by Bio Medic Data Systems, Inc. include a coil antenna coupled to an integrated circuit (IC) chip. The chip includes a memory and a thermistor. Circuitry is provided for receiving an interrogation signal, deriving power from the interrogation signal, deriving timing clocks from the interrogation signal, and controlling the memory and the thermistor to output data stored in the memory or temperature information sensed by the thermistor to the interrogator. It is also known in the art to program input data to the on-board memory of the transponder.

This prior art transponder has been satisfactory. However, it suffers from the disadvantage that the integrated circuitry required too much power for operation in the READ MODE. This resulted in the reduced read distance between the transponder and interrogator. The memory, which included an EEPROM was too small and the temperature data was required to be transmitted over the top of sixteen of the memory bits making them unusable. Although the prior art taught locking the data in the memory to preserve the integrity of the memory, the lock was permanent and could not be selectively changed by the transponder user as needed. Furthermore, in the prior art, synchronization between the transponder and interrogator has been performed utilizing a preamble of the transponder's data signal. Because the entire data signal was required to be transmitted as well as the preamble during any synchronization process, time was wasted, slowing down the overall programming and/or read cycle. Furthermore, a single temperature reading taken by the transponder was sent to the interrogator and used as the temperature. Many factors can affect the reading and recording of temperature in a transponder so that there would be fluctuations between successive temperature readings. In effect, a floating temperature value would occur reducing the precision of the temperature read. Lastly, during programming, utilizing conventional signal encoding techniques, the timing of the signal transmitted between the transponder and interrogator was critical. However, because timing was so critical, noise or other environmental factors could readily disrupt the signal, damaging the results.

Accordingly, an implantable programmable temperature transponder which overcomes the shortcomings of the prior art is desired.

SUMMARY OF THE INVENTION

An implantable programmable temperature transponder includes a receiver for receiving a programming signal. A memory has a plurality of addresses therein. The data being separated into two portions, a data storage portion and a lock portion, the data portion being capable of storing a plurality of subsets of bits, each subset of bits corresponding to a character. The lock portion stores a plurality of locks, each lock corresponding to a respective subset of bits corresponding to each character. An address module addresses each address within the memory. A data module receives data to be programmed and stores data in the memory at the address selected by the address module; the lock section allowing storing of data in the memory at the selected address if the corresponding lock is clear and preventing storing of data in the memory if the corresponding lock is set.

In a preferred embodiment, the implantable programmable temperature transponder includes a comparator for comparing a programming signal with a reference voltage and outputting a comparison signal in response thereto. A transmitter receives the comparison signal and outputs a first indicator signal if the received voltage is less than the reference voltage and outputs a second signal if the input voltage is greater than the reference voltage; the first signal being the inverse of the second signal for indicating to the interrogator the sufficiency of the input programming signal. The programming signal may be pulse space modulated.

In a preferred embodiment, the implantable programmable temperature transponder includes a clock generator for enabling current to be supplied to the memory during programming, turning off the current to the memory after each successive address has been addressed.

A temperature module including a thermistor is coupled to the data module. The temperature module includes a free-running counter which is continuously counting the output of the thermistor. A clock generator counts predetermined periods, the current count of the temperature module counter being latched and output to the interrogator at the end of each period. The interrogator receives a number of these counts, and determines the difference between successive counts to obtain a plurality of actual count numbers having occurred in each elapsed time period. These actual counts are then aggregated. The aggregate value of the differences is divided by the total time for obtaining the number of samples to obtain an average count per time or frequency. Knowing the thermistor's inherent relationship between frequency and temperature, the temperature corresponding to that frequency is known and is output by the interrogator as the temperature.

Accordingly, it is an object of the invention to provide an improved implantable temperature transponder.

Another object of the invention is to provide a transponder which minimizes power used during programming and reading of the transponder.

A further object of the invention is to provide a transponder which speeds up the voltage synchronization process with an interrogator.

Yet another object of the invention is to provide a transponder with expanded memory and the ability to transmit temperature data separately from the data stored in memory so that all the memory addresses can be used.

Another object of the invention is to provide a more precise temperature reading.

Still another object of the invention is to provide a memory which provides varying levels of memory protection including the ability for the transponder user to selectively lock the data stored in the memory.

Still other objects and advantages of the invention will in part be obvious and will in part be apparent from the specifications and drawings.

The invention, accordingly, comprises the features of constructions, combinations of elements, combinations of steps, and arrangement of parts which will be exemplified in the construction as hereinafter set forth and the scope of the invention will be indicated in the claims.

BRIEF DESCRIPTION OF THE DRAWINGS

For a filler understanding of the invention, reference is had to the following description in connection with the accompanying drawings, in which.

DETAILED DESCRIPTION OF THE PREFERRED EMBODIMENTS

Figure 1:
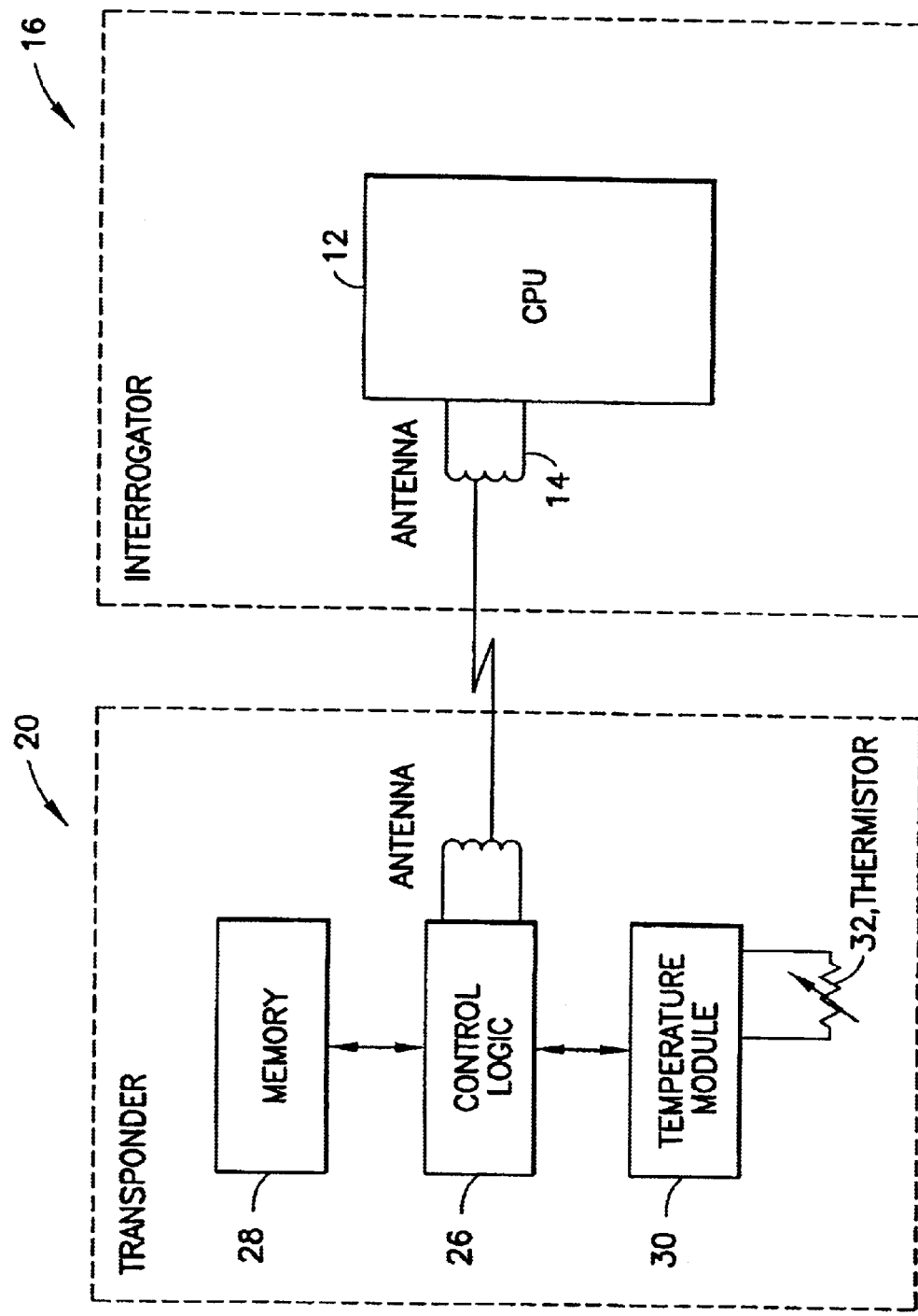
FIG. 1 is a block diagram of an interrogator/transponder system.

Reference is first made to FIG. 1 in which an interrogator, generally indicated as 10 and a transponder generally indicated as 20 are shown. Interrogator 10 and transponder 20 communicate with each other through inductive coupling as known in the art from U.S. Pat. No. 4,730,188. As will, be discussed below, interrogator 10 provides a signal to transponder 20 which provides power to transponder 20, a clock signal and an operational command such as enter the PROGRAM MODE or TEMPERATURE MODE. Transponder 20 sends a return signal containing information therein to interrogator 10 as is known in the art.

Interrogator 10 includes a CPU 12 for generating command/power/clock signals (collectively interrogator signals) in response to the user inputs. These signals are input to an antenna 14 for broadcast to transponder 20.

An antenna 22 within transponder 20 receives the interrogator signal from interrogator 10 and inputs a 364 kHz signal to a rectifier 24 (FIG. 2) which receives the AC signal from the antenna 22 and rectifies the signal. The rectified signal is then passed to a control logic circuit 26 which, in response to the rectified interrogator signal will either read out data from the memory 28, program data into a memory 28, or read out temperature data from a temperature module 30. Temperature module 30 includes a thermistor 32 which changes resistance levels in response to changes in temperature which can be converted into a frequency as is known in the art, the frequency changing as a function of temperature. The temperature data and data from memory 28 are output under the control of control logic 26 through a modulator 34 for modulating the signal as known in the art to be transmitted by antenna 22 back to interrogator 10 where the data is operated upon by CPU 12 of interrogator 10.

Figure 2A:
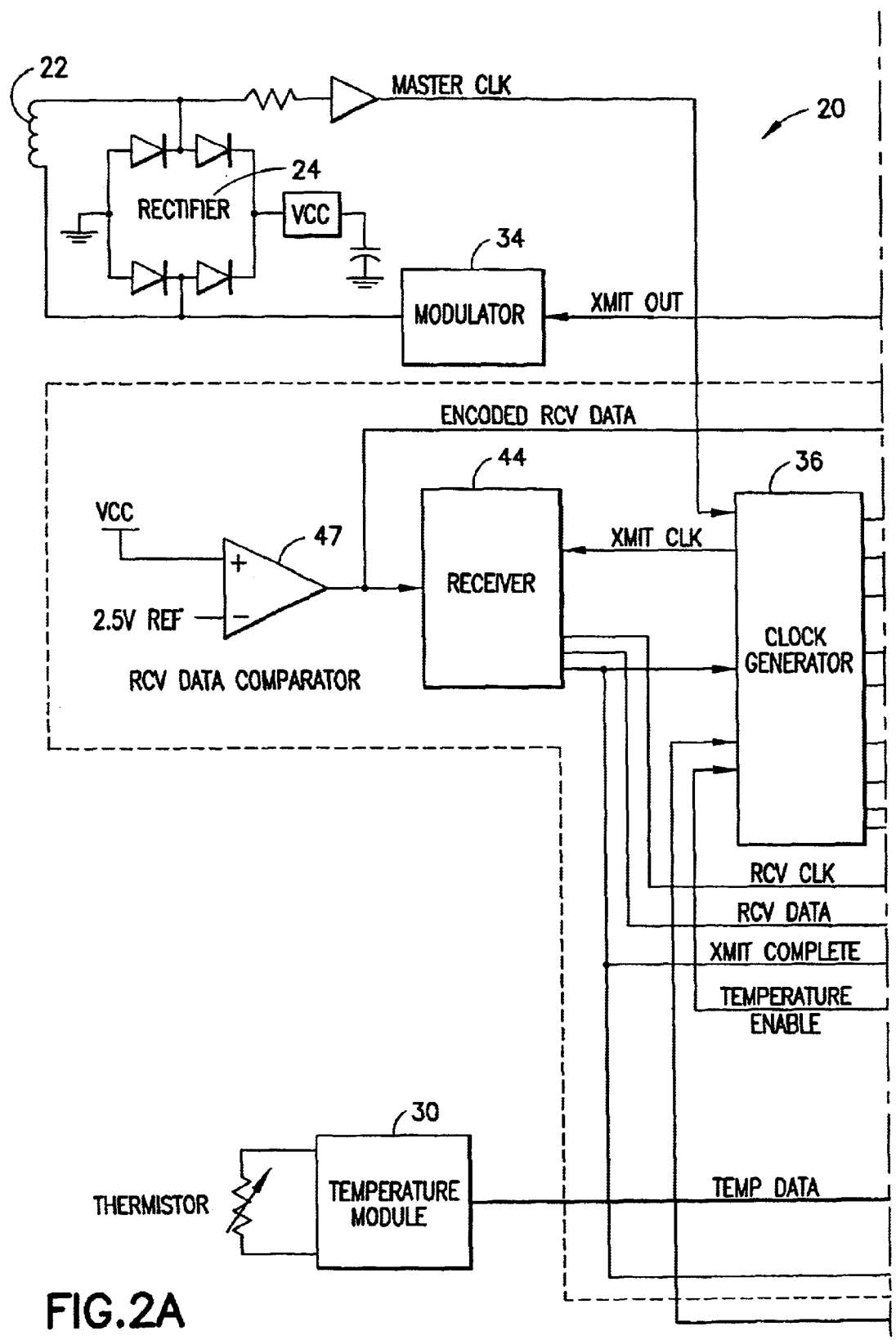
FIG. 2 is a more detailed block diagram showing the transponder control logic constructed in accordance with the invention.
Figure 11:
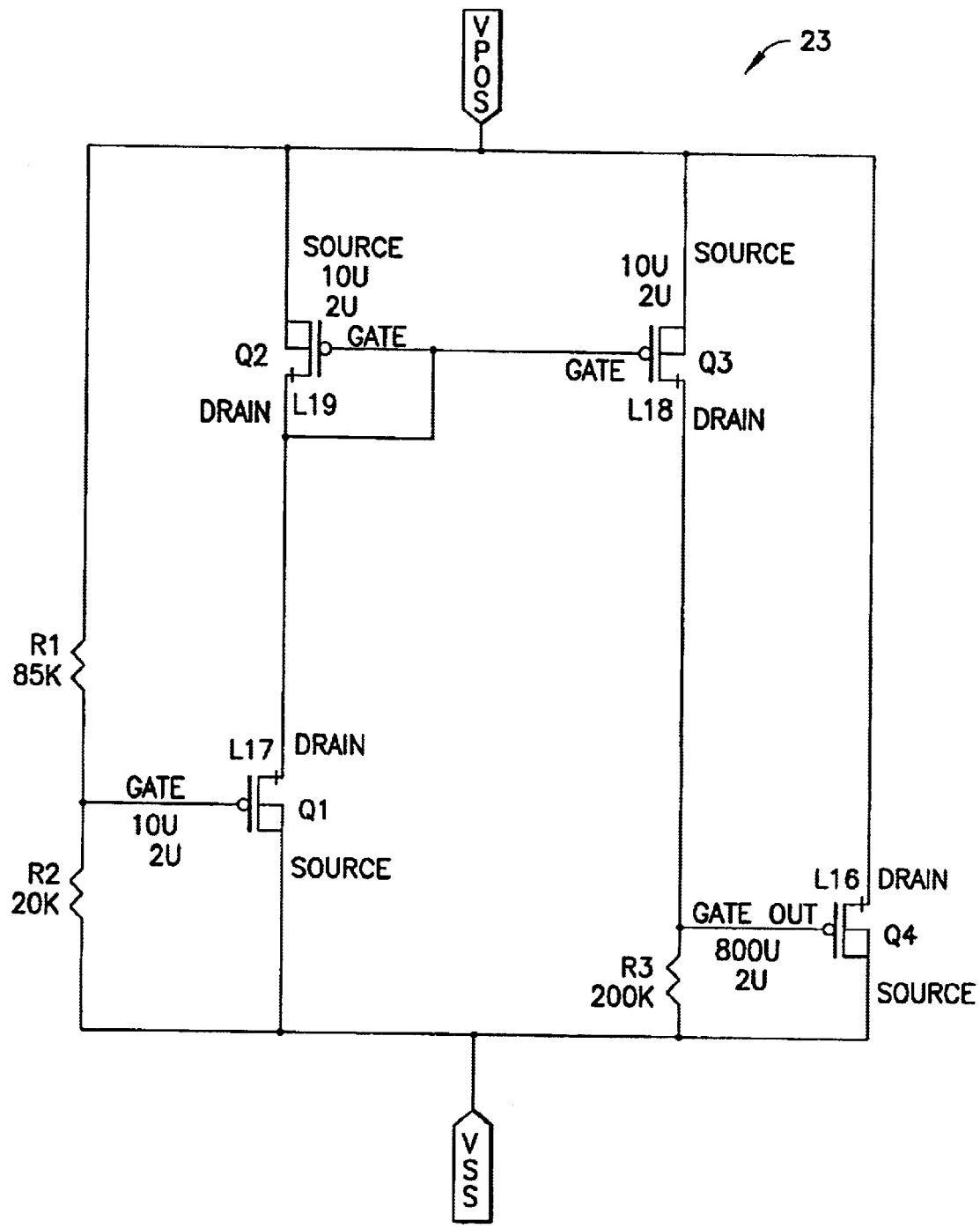
FIG. 11 is a circuit diagram of a clamp circuit constructed in accordance with the invention.

Reference is now made to FIG. 2 and FIG. 11 in which a block diagram showing the circuitry of transponder 20, and in particular control logic 26, in greater detail is provided. The rectifier 24 includes a diode arrangement for rectifying the input signal and a clamp 23 for regulating the voltage level VDD to the transponder components of finish Clamp 23 simulates the behavior of a Zener diode. Clamp 23 includes four metal oxide semiconductor field effect transistors (MOSFETs) Q1–Q4, resistors R1–R3, and voltage connections Vpos and Vss. In effect, the electronic circuit is a MOSFET Zener circuit providing IC protection to the remainder of the transponder circuitry by clamping the voltage. The MOSFET Zener clamp 23 connects Vpos to the incoming positive voltage power supply and connects Vss to ground.

In clamp 23, transistors Q1 and Q4 are N-channel MOSFETs, while transistors Q2 and Q3 are P-channel MOSFETs. Transistor Q4 must be much larger in size than transistors Q1–Q3 because it must be able to pass a large amount of current from Vpos to Vss. In a preferred embodiment, transistor Q4 is at least twenty times larger than the other MOSFETs.

As shown in FIG. 11, resistor R1 is connected at one end to Vpos and at the other end it is connected to the gate of transistor Q1 and to resistor R2. Resistor R2 is connected at one end to the gate of transistor Q1 and resistor R1 and at its other end is connected to Vss. Resistor R3 is connected at one end to the gate of transistor Q4 and the drain of transistor Q3 and the other end is connected to Vss. The gate of transistor Q1 is connected to resistors R1, R2 while the source of transistor Q1 is connected to Vss and the drain is connected to the gates of transistors Q2, Q3 and the drain of transistor Q2. The gate of transistor Q2 is connected to the gate of transistor Q3, the drain of transistor Q1 and its own drain. The source of transistor Q2 is connected to Vpos and the drain of transistor Q2 is connected to the drain of transistor Q1 and the gates of transistors Q2, Q3. The drain of transistor Q3 is connected to resistor R3 and the gate of transistor Q4. The drain of transistor Q4 is connected to Vpos.

During operation, resistors R1, R2 act as a voltage divider and control clamp threshold voltage. When the voltage on the gate of transistor Q1 rises, transistor Q1 will turn on, allowing current to pass through its drain and source. Transistors Q2, Q3 act as a current mirror so that whatever current is on the drain of transistor Q2 is the same amount of current on the drain of transistor Q3. With a current on the draw of transistor Q3 and resistor R3, a voltage will be present on the gate of transistor Q4. The value of transistor R3 determines the gain of the device. In other words, with a large value for resistor R3, the voltage on the gate of transistor Q4 rises faster than the voltages at Vpos. The value of transistor R3 then controls the speed at which the clamp acts.

As the voltage rises on the gate of transistor Q4, it will turn on, allowing current to pass through the drain and source. When transistor Q4 dumps current from Vpos to Vss, this keeps the voltage of Vpos at a constant level thereby clamping the supply voltage to the remainder of the integrated circuit, protecting the integrated circuit from a damaging over voltage condition. In a preferred embodiment transistor Q1 will start to turn on at approximately four volts and transistor Q4 will turn on and dump enough current to limit Vpos to approximately five volts.

Clamp 23 limits the supply voltage for the rest of the integrated circuit. Usually, integrated circuit devices do not need voltage limitation as integrated circuit devices are used with a controlled power source. In other words, the range of voltage that must be supplied to the chip and any regulation or limitation of power is done off chip. On the other hand, because the transponder is powered by an interrogator which provides an unknown voltage level to the interrogator, the protection from an over voltage condition is supplied on chip by the clamp.

The antenna signal serves as a master clock input to a clock generator 36. Clock generator 36 divides down the master clock signal and provides timing signals and enabling signals to a data module 40, address module 38, and memory 28.

Control logic 26 includes address module 38 for receiving signals from the clock generator and addressing an identified address within memory 28 in response to the clock generator signals. A data module 40 receives latch signals from clock generator 36, data from memory 28, temperature data from temperature module 30 and outputs data in response to these signals to a transmitter 42. Transmitter 42 transmits an output signal containing the data through modulator 34 which modulates the antenna 22 according to the output signal output by transmitter 42.

A receiver 44 receives the data signal output by interrogator 10 after processing by a comparator 47 and outputs the received data to address module 38. A program control 46 receives data from memory 28 and a program bit from data module 40, an address from address module 38 and in response thereto outputs a program enable signal to clock generator 36 which in turn enables the programming of data in memory 28.

As described below, comparator 47 also acts as a voltage synchronization circuit and receives the interrogator signal and compares the interrogator signal to a reference voltage; 2.5 volts by way of example. The comparator outputs a signal in response to the received interrogator signal and outputs the signal to the transmitter 42 which, in turn, outputs the signal through modulator 34 to antenna 22 to be transmitted to interrogator 10.

Figure 3:
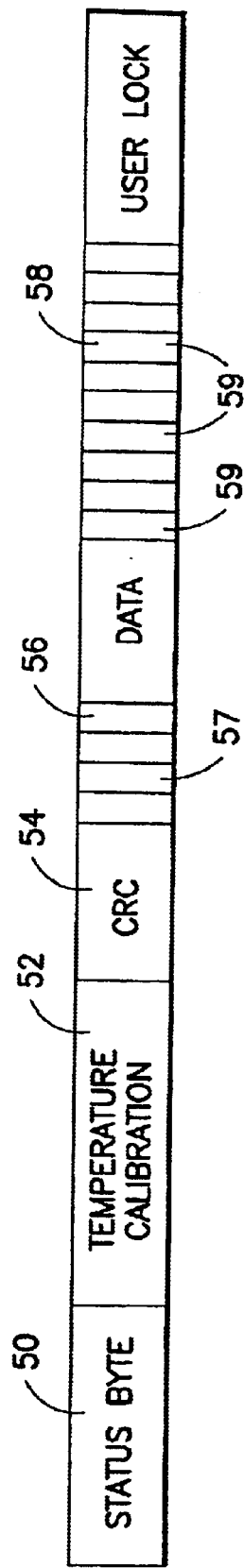
FIG. 3 is a schematic diagram showing a format for the memory constructed in accordance with the invention.

As shown in FIG. 3, in a preferred embodiment, memory 28 is an EEPROM. Memory 28 is structured so as to have a status byte region 50, a temperature calibration region 52, a CRC region 54, a data region 56, and a user lock region 58. Temperature calibration region 52 includes a temperature adjustment value which is the offset between the calculated or sensed temperature sensed by temperature module 30 and the actual temperature of whatever is being monitored. The data stored in temperature calibration portion 52 is output to interrogator 10 along with temperature data from temperature module 30 and interrogator 10 through CPU 12 calculates the actual temperature as is known in the art.

CRC region 54 is an integrity check for the data stored in memory 28 as is known in the art, utilizing standard polynomial equations to compare and verify the data in memory.

Data region 56 stores user programmable information input from interrogator 10 while in PROGRAM MODE as discussed below and read from the memory during READ MODE. The data is stored as bits 57 which in combination represent characters. In a preferred embodiment, the least significant character is stored with the least significant bit of the character starting at the least significant bit in the least significant byte of data region 56 and goes upwards to the most significant bit of the character and the most significant bit in the most significant byte of data region 56. A number of bits 57 corresponds to a character. In a preferred embodiment, utilizing the compression techniques, each character can be represented by less than one byte. In a preferred embodiment, the data portion stores enough data to represent 32 characters formed as a plurality of discrete subsets of bits 57 in data region 56.

User lock region 58 is divided into bits 59. Each bit corresponds to a character stored in data region 56. Each bit represents the lock state of the respective character in the data. For example, if a zero is stored in the least significant bit of the user lock region which corresponds to the bits corresponding to the least significant bits for the least significant character stored in data region 56 then the lock is "clear". The user lock bit is "set" by storing a one in the desired bit of user lock region 58. For example, if the character data is stored as bytes, the least significant bit of the least significant byte of user lock region 58 corresponds to the least significant character in data region 56 and the most significant bit of the most significant byte corresponds to the most significant character. It should be noted that any other mapping arrangement of lock bits to character bits may be used.

Figure 4:
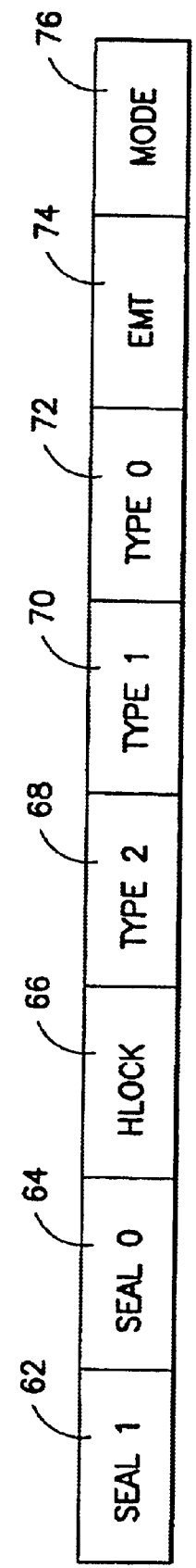
FIG. 4 is a schematic diagram showing a format for the status byte of the memory format constructed in accordance with the invention.

As shown in FIG. 4, status byte 50 includes information for controlling the operation on memory 28. Status byte 50 includes a mode bit 76 which causes the transponder to operate on all of its internal memory or just a portion thereof. This bit directly provides an output to the program control 46 and, in effect, is "hard wired" to automatically control the transponder circuitry. Specifically, as discussed in detail below, if mode bit 76 is clear, i.e., contains a zero therein, then the transponder will transmit or read from all of memory 28. If mode bit 76 is a one, then transponder 20 may only read from or program into a portion of memory 28 such as the first half of memory 28.

Bits 68 through 74 collectively indicate to the interrogator and transponder the type of transponder that transponder 20 is. For example, if there is an extended memory within transponder 20, then a one may be stored in bit 74 to indicate that transponder 20 is an extended memory transponder (EMT). Bits 68, 70, and 72 may further identify the transponder type such as a laboratory transponder or industrial use transponder to determine a transponder data format most suitable for its intended purpose. Bits 68 through 74 are not hard wired, and therefore are not automatically input to program control 46. Bits 68–74 may also be addressed and reprogrammed by address module 38 and data module 40 to conform transponder 20 to the user's needs.

An HLOCK bit 66 causes program control 46 to disable clock generator 36 in the PROGRAM MODE if the HLOCK bit is set (i.e., has a value of one). If the HLOCK is clear, i.e., has a value of zero, then programming can occur. By disabling the clock generator 36, no data can be written to the address module 38 and data module 40 into memory 28. This bit 66 is hard wired to program control 46 and controls programming of all of the characters in temperature calibration region 52, CRC region 54, data region 56, and user lock region 58 not selective characters in data region 56 like user lock 58. The HLOCK bit can be addressed and reprogrammed utilizing address module 38 and data module 40 as discussed below, and is used to prevent accidental or inadvertent overwriting of the data in memory 28.

SEAL lock bits 62, 64 hold two bits in combination which can act to seal transponder 20 from any future re-write, making the transponder a permanently read-only transponder. Bits 62, 64 are also hard wired to program control 46 and cause clock generator 36 to be disabled in the PROGRAM MODE. However, unlike the HLOCK bit 66, SEAL bits 62, 64 are not reprogrammable once they are set. To seal the transponder, SEAL 0 should be set during a first write command and on a second write process SEAL 1 should then be set.

It should be noted that the format described above from least significant bit to most significant bit and the relative placement of the different memory regions is by way of example. The individual bits can be arranged in any order as long as one group of bits stores data, one group of bits is mapped to the data bits to act as a lock, and one group of bits acts to prevent programming of the data region as a whole.

The clamp 23 is entirely built, utilizing a CMOS Process, into the integrated circuit devices. Normally, integrated circuit devices such as clamp 23 are built using a bipolar process. A mixed process of bipolar/CMOS is not feasible in making the integrated circuit yet a Zener Diode is still needed in the integrated circuit so that the MOSFET Zener Diode formed from the CMOS process is used instead.

READ MODE

When a continuous voltage signal is received from interrogator 10, clock generator 36 utilizes the interrogator signal as a master clock and outputs a READ EEPROM signal to memory 28 and an INCR ADDR signal to address module 38 which causes address module 38 to sequentially latch the addresses of the memory 28 along the address bus. This causes the addressed data to be output along a DATA BUS to data module 40 where it is then output as a DATA OUT signal to transmitter 42. Transmitter 42 then outputs the data to modulator 32 which outputs a modulated signal to interrogator 10 through antenna 22. Clock generator 36 continuously provides a clock to address module 38 to increment the address being latched by address module 38 while in the READ MODE.

During the READ MODE, clock generator 36 provides a READ EEPROM signal to memory 28. As READ EEPROM signal is input to memory 28, memory 28 is utilizing current. However, during operation of a preferred embodiment, the READ EEPROM signal is output to memory 28 only while address module 38 latches the address in memory 28 and data is output to data module 40. Once the data is output along the DATA BUS, the READ EEPROM signal is disabled until clock generator 36 outputs a successive INCR ADDR signal to increase the address to be addressed by the address module 38. The READ EEPROM signal is then enabled and current is supplied to memory 28 to allow reading of data in memory 28 and this process is repeated until the READ MODE is terminated when power is removed from transponder 20. By cutting off the current supply to memory 28, the overall current consumed during the READ MODE is lowered. Because the memory is in EEPROM, i.e., a static memory, the data is stored even in the absence of current being supplied to memory 28.

Clock generator 36 outputs a PREAMBLE ENABLE signal to transmitter 42 causing transmitter 42 to output a preamble as is known in the art. After a predetermined time period sufficient to output the preamble, clock generator disables the preamble and outputs a DATA ENABLE signal to transmitter 42 causing transmitter 42 to output the DATA OUT signal containing the data from data module 40 so that during the READ MODE, the output of transponder 20 is a preamble followed by the data read from memory 28 which has been modulated by modulator 34. Once a complete cycle of the DATA OUT signal has been output by transmitter 42, clock generator 36 disables the DATA ENABLE and outputs the PREAMBLE ENABLE signal.

PROGRAM MODE

Figure 6:
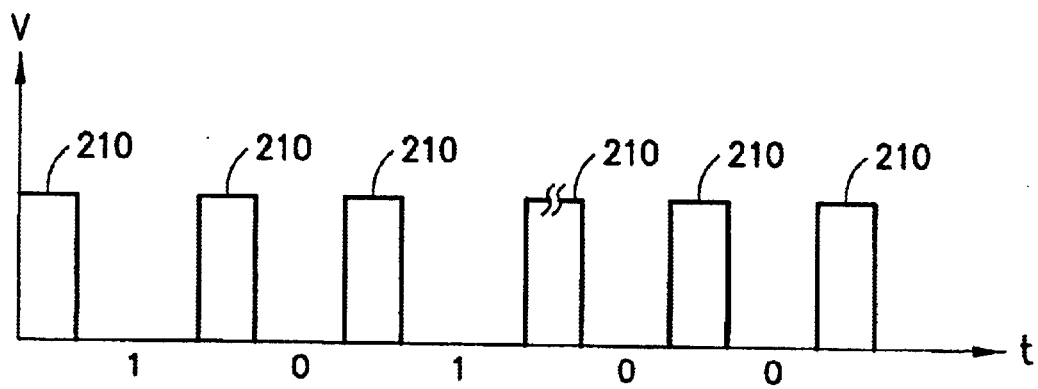
FIG. 6 is a timing diagram of a programming signal output in accordance with the invention.
Figure 7:
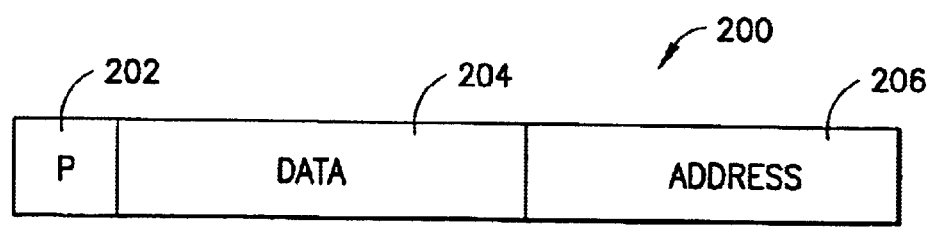
FIG. 7 is a schematic diagram of a format for the content of the programming signal.
Figure 8A:
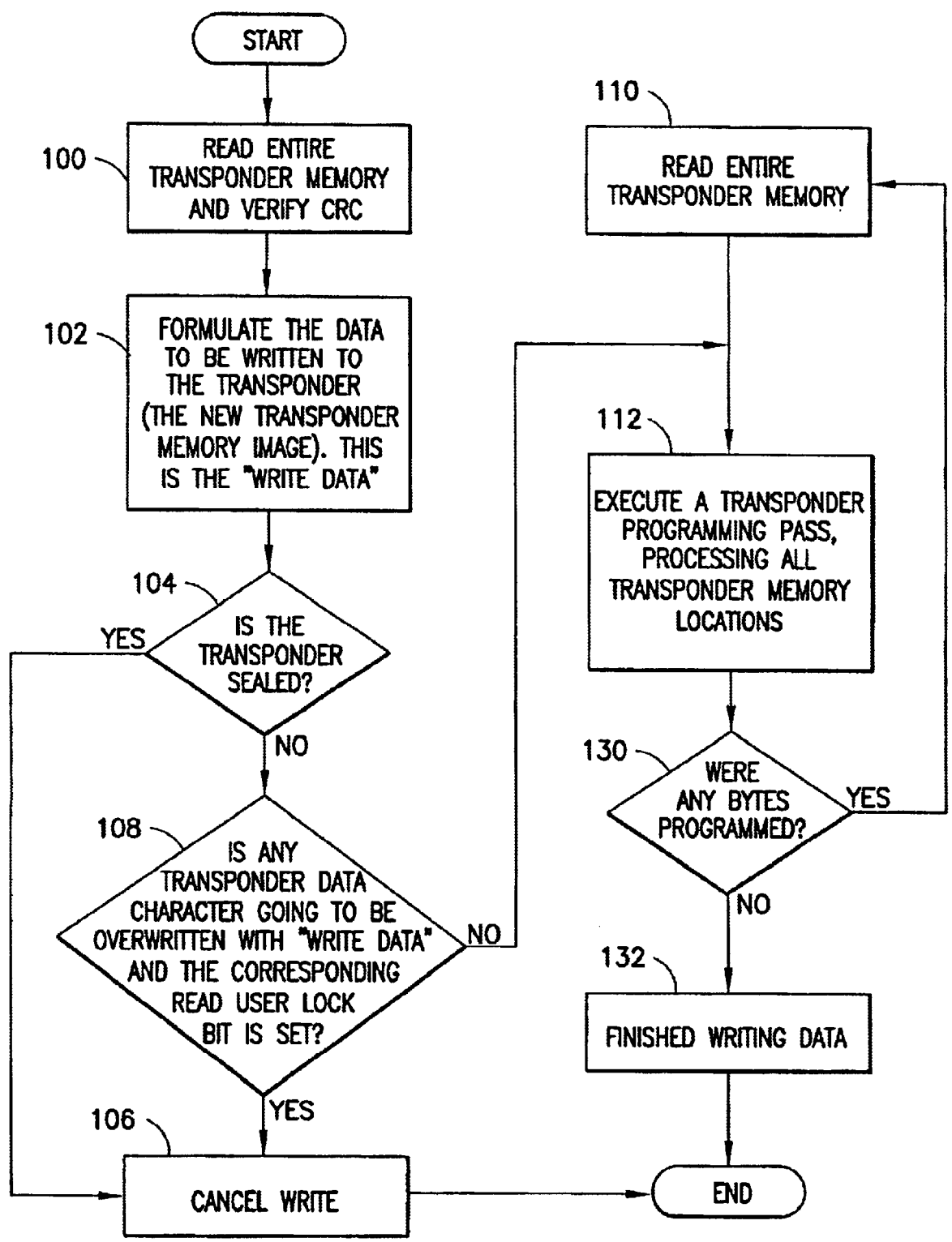
FIGS. 8(A), 8(B) are flow charts showing the method for programming the transponder in accordance with the invention.

Reference is now also made to FIGS. 6–8 in which the operation of the PROGRAM MODE is illustrated. In order to begin programming, transponder 20 is first read in the READ MODE and the data is verified using data in CRC region 54 of memory 28 in a step 100. Transponder 20 then transmits the data stored in memory 28 as discussed above. Interrogator 10 will then power down antenna 14, in effect turning off transponder 20. Interrogator 10 will then formulate the data to be written into memory 28, i.e. programmed into status byte 50, temperature calibration region 52, CRC region 54, data region 56 or user lock region 58 in a step 102. Interrogator 10 formulates a data string corresponding to each bit of memory 28, even if that bit is not to be reprogrammed. Interrogator 10 utilizing CPU 12 will then analyze the data stored in memory 28. The interrogator will analyze status byte 50 to determine whether or not bits 62, 64 of status byte 50 are set in a step 104. If status bytes 62, 64 are set, then programming is canceled by the interrogator in a step 106.

In a step 108 it is determined whether any bits 57 in data region 56 to be overwritten (reprogrammed) has a corresponding bit 59 in user lock region 58 which is set. If so, then this indicates that the character is not to be changed unless the user lock bit 59 is cleared so writing is canceled in step 106. A separate programming signal must then be sent to clear the user lock.

If the user lock bit 59 corresponding to a character to be reprogrammed is not set then a transponder programming pass for processing all memory locations in memory 28 is performed in a step 112.

Figure 8B:
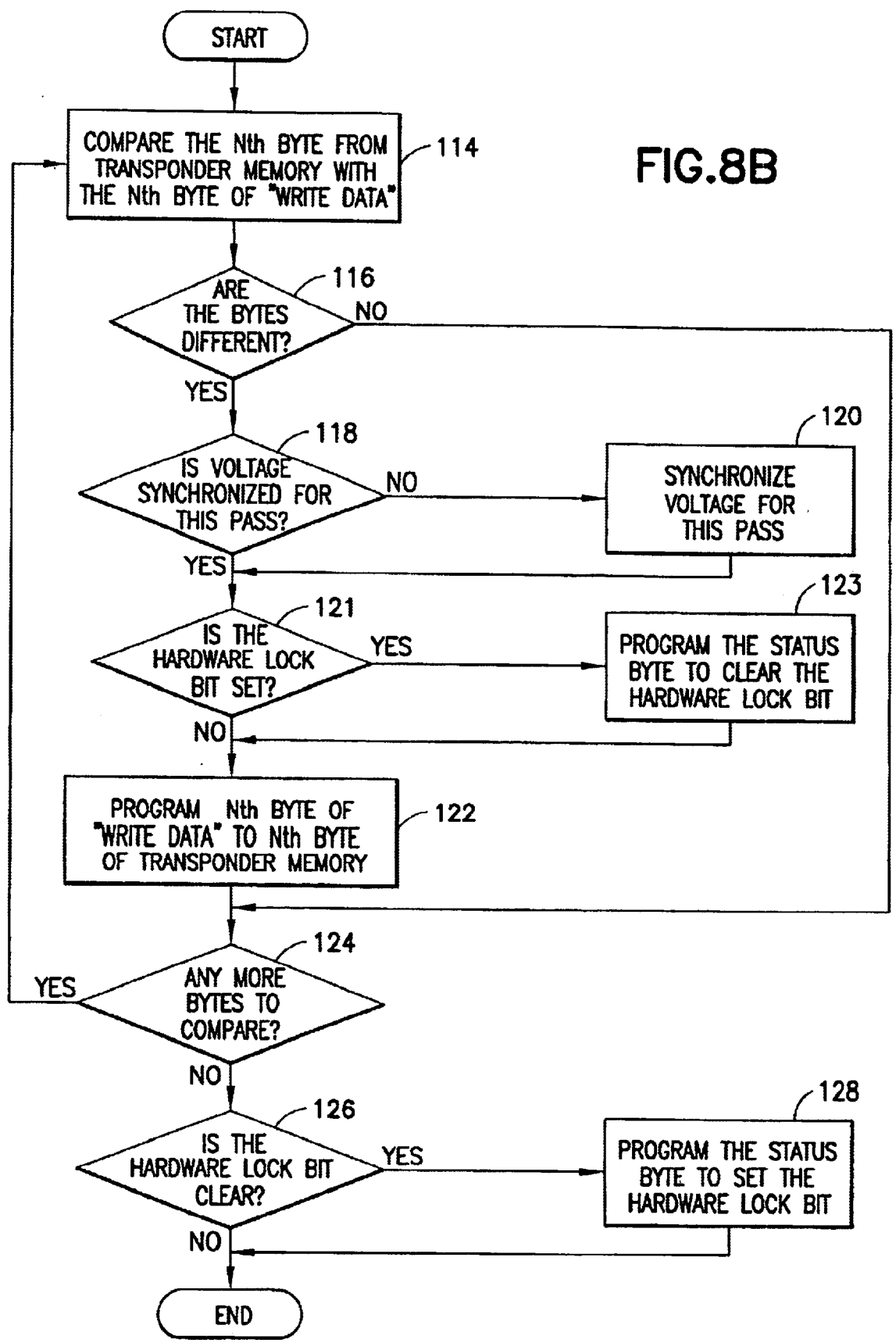

Reference is now made to FIG. 8(B). The Nth byte (or subset of bits) of data (corresponding to a character) stored in data region 56 is compared with the Nth byte of the write data in a step 114. If the bytes are the same as determined in a step 116, there is no need to reprogram memory 28 at that data region address and it is determined whether any more bytes are required to be compared in a step 124.

If the bytes are different as determined in step 116 then in a step 118 it is determined whether the voltage has been synchronized and if not, voltage synchronization is performed in a step 120. The interrogator and the transponder must first confirm that there is sufficient voltage level for the interrogator signal as received at the transponder for the transponder to properly operate. In an exemplary embodiment, this voltage level is determined to be 2.5 volts. In other words, the signal from the interrogator must produce at least 2.5 volts at the transponder in order to effectively transmit data to the transponder and the 2.5 volt threshold may be used to determine the difference between a zero signal value and a one signal value.

In order to transmit data to the transponder 20, interrogator 10 must determine what output power level will produce the reference voltage at the transponder. This relationship will change as the distance between the interrogator 10 and transponder 20 changes. Transponder 20 assists interrogator 10 in determining this power level by sending feedback in the form of transmitted data that the interrogator 10 can read. The feedback tells interrogator 10 whether the voltage at transponder 20 is presently above or below the threshold voltage.

Figure 5:
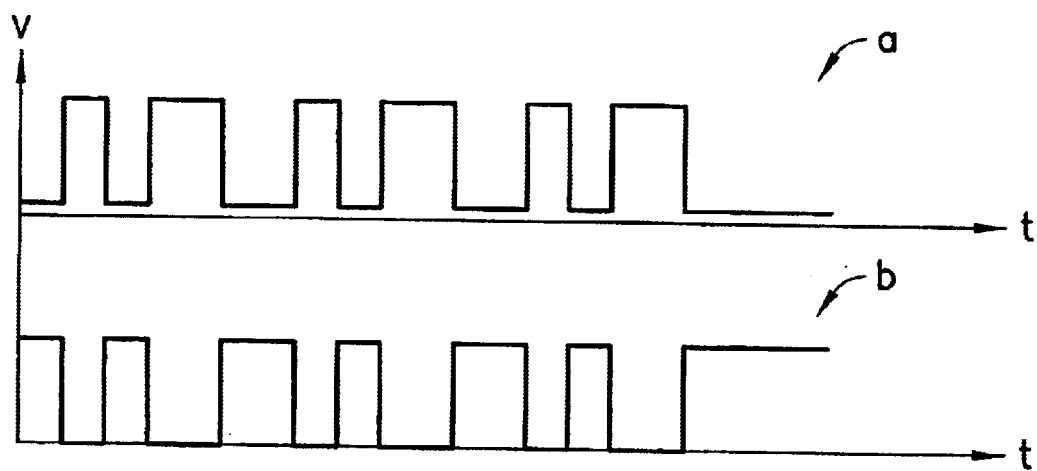
FIG. 5 is a timing diagram of a voltage synchronization indication signal sent by the transponder to the interrogator in accordance with the invention.

In step 120 interrogator 10 sends a signal which powers up transponder 20. The interrogator signal is received at antenna 22 and input to comparator 47 where the interrogator signal is compared with a reference voltage REP. By way of example, if the interrogator signal is greater than the reference voltage, comparator 47 outputs a high signal. Conversely, if the received signal is less than the reference voltage, comparator 47 will output a low signal. Comparator 47 outputs an ENCODED RCV DATA signal which is input to transmitter 42. In a preferred embodiment, transmitter 42 will output a first signal a as shown in FIG. 5 if the transponder voltage is below the reference voltage and a second signal b shown in FIG. 5 if the transponder voltage is above 2.5 volts.

If the pattern received by interrogator 10 indicates that the input voltage is above the desired threshold, i.e., signal b, interrogator 10 reduces the power output and the process is repeated until a pattern indicating below the threshold is received by the interrogator. Once signal a, which is the inverse of signal b, is output, indicating to interrogator 10 that the voltage received is below the threshold voltage after an adjustment, the power output by interrogator 10 would be increased. This process is repeated until the adjustment required from the interrogator is too fine, i.e., beyond the capabilities of the interrogator to further adjust above or below the threshold voltage. In an alternative embodiment, once an adjustment has become too fine, transponder 20 outputs a signal to interrogator 10 to discontinue adjustment.

By changing the output power level and monitoring the feedback signal, interrogator 10 can deduce the output power level that produces the threshold voltage (2.5 volts) at transponder 20. Once this threshold level is determined, interrogator 10 is able to transmit data to transponder 20 because it knows how to produce an output power that will result in a voltage greater than 2.5 volts at the transponder and conversely it knows the output power that will produce less than 2.5 volts at transponder 20. Transponder 20 translates a voltage of less than a threshold voltage as a zero logic state and a voltage greater than the threshold voltage as a one logic state. Transponder 20 powers up in the feedback mode so that interrogator 10 can quickly determine the threshold voltage transition level. If, however, interrogator 10 is not interested in programming the transponder, it can simply set a constant output power level and wait until transponder 20 switches to the READ MODE and read data from transponder 20.

Once the voltage has been synchronized in step 120 it is determined whether HLOCK bit 66 has been set in step 121. If so, then HLOCK bit 66 must be cleared to permit programming in a step 123. In step 123 a program signal is sent by interrogator 10 to clear HLOCK bit 66.

The program signal has a data format as shown in FIG. 7 in which program signal 200 has a program region 202, a data region 204, and an address region 206. The program region 202 is a single bit, in a preferred embodiment, indicating that the signal is, in fact, a program signal. The data region 204 includes the data to be programmed into memory 28 and represents a single character. In a preferred embodiment each character is one byte in length and data region 204 is made up of 8 bits, and with compression techniques each character can be represented by less than eight bits, while the data region can remain 8 bits long to program two bits for example if compressed to six bits, of a successive character. Address region 206 contains the data for indicating the address at which the data of the data region 204 is to be written and in a preferred embodiment is five bits.

As shown in FIG. 6, the actual signal transmitted by interrogator 10 which embodies the data of data signal 200 is pulse space modulated. FIG. 6 is a timing diagram of an exemplary signal. In prior art inductively coupled transponders, the communication between the interrogator and the transponder was heavily dependent upon the timing of the transmit and receive signals between the two. The signal in the present invention is timing independent. The signal is made up of a series of fixed or standard pulses 210, the width or spacing between these pulses is modulated by a delay to correspond to the desired data. For example, a zero may correspond to a standard spacing between two pulses 210 while a data 1 is represented by a delayed or elongated spacing between adjacent pulses 210. As a result, timing is no longer a factor. The end of a data transmission cycle may be indicated by remaining in a logic level for a predetermined period of time corresponding to more than the standard pulse or the value of a logic zero or logic one. This is how programming starts in a step 122.

Receiver 44 receives the data as well as a transmit clock from clock generator 36. If receiver 44 detects the leading edge transition of a pulse 210, it then begins comparing the space between the pulses with a count dependent upon the XMIT CLK signal from clock generator 36, for example, eight cycles of the transmit clock. If the received pulse width is less than the transmit clock, then, by way of example, the receiver will determine that the derived data is a zero and transmit that zero to the address module 38 as the RCV DATA signal along with a RCV CLK signal for clocking the data into the address module 38. On the other hand, if the length of the width of the space is longer than the counted cycles of the transmit clock, it determines that the received data is a one and will transmit a one to address module 38 along with a RCV CLK signal for clocking the data into address module 38. If the detected pulse has a width greater than a predetermined number of cycles, then receiver 44 determines that the data transmission has been completed and a XMIT COMPLETE signal is input to address module 38. As the data is shifted into address module 38, it is then shifted as RCV DATA SEQUENCE signal to data module 40 so that the first 8 bits, by way of example, corresponding to data portion 204 of the data signal are latched in data module 40. Additionally, the program bit of program region 202 is output to program control 46 to indicate programming is to occur.

If interrogator 10 does not have a CPU 12 with the software capability for determining that the data has been locked by a comparison of the read data stream, programming will still be prevented by an interrogator because of program control 46. When all of the data has been received by receiver 44, the program bit has been received by program control 46, program control 46 looks at the status byte 50 of memory 28 and determines whether or not the seal bits 62, 64 of status byte 50 have been set. If seal bits 62, 64 have been activated, program control 46 will not output a PROGRAM ENABLE signal to clock generator 36. Clock generator 36 will not clock the address module 38 or data module 40. Therefore, the programming cannot be forced by the interrogator.

If either one of seal bits 62, 64 are clear in this embodiment, program control 46 then looks to HLOCK bit 66 which is also hard wired into program control 46. If HLOCK bit 66 has been set then again the program control 46 will not output the PROGRAM ENABLE signal to begin programming as determined in a step 121.

Because HLOCK bit 66 is reprogrammable, in step 123 program control 46 determines whether or not the address indicated by address module 38 along the address bus corresponds to the status byte 50 of memory 28. If the address indicated by address module 38 is the status byte, program control 46 outputs a PROGRAM ENABLE signal to clock generator 36. If the address is not the status byte, then it will not enable clock generator 36 preventing programming of any of the temperature calibration region 52, CRC region 54, remaining bits of the data region 56 or user lock region 58.

In step 123, interrogator 10 outputs program signal 200 containing the address of status byte 50 in address region 206 and a zero for bit 66 in data region 204. Because the address of the programmed byte is the status byte, program control 46 outputs a PROGRAM ENABLE signal to clock generator 36. Clock generator 36 clocks the address module along the ADDR LATCH input to clock the status byte address causing it to send a signal of the specific address of memory 28 and also outputs a LATCH DATA signal to data module 40 which causes data module 40 to shift data 204 of data signal 200 into memory 28 at the address indicated by address module 38. This, in effect, will unlock the HLOCK bit 66 by placing a zero in HLOCK bit 66.

Once HLOCK bit 66 has been cleared in step 123, or if it was determined that HLOCK bit 66 was clear in step 121, in a step 122 the Nth byte of write data is programmed into the transponder in a manner identical to programming the HLOCK. Program control 46, after confirming that the HLOCK bit 66 is clear, outputs a PROGRAM ENABLE signal which causes clock generator 36 to clock address module 38 to address the desired memory address as indicated by the data stored in address region 206 of data signal 200. The data of data region 204 latched into data module 40 is input to memory 28 at the indicated address. It is then determined in a step 124 whether there are any more bytes to compare in a step 114.

If there are no more bytes to compare, then for safe keeping, although optional, the HLOCK bit 66 is programmed to be set by first determining if the bit is clear in a step 126. If the bit is clear it is programmed to be set in step 128. Again, programming is the same as that in step 123 only the value of the data being changed in bit 66 is different. In a step 130 it is determined whether any bytes are programmed.

If bytes from memory 28 have been programmed, then the transponder is again read in step 110 and the data read from the transponder is compared with the data that was to be programmed by the interrogator 10 under the control of CPU 12. If any bytes are different, then transponder 20 would be reprogrammed to correct those differences in a step 112. If there are no differences between the bytes of data stored as compared to the bytes of data intended to be programmed, then programming is finished in a step 132, which would be arrived at by determining that in a second go around, no bytes were again programmed in step 130.

If, in step 108 it is determined that one or more user lock bits 59 corresponding to a character is set, a separate programming signal must be sent to clear the user lock. User lock region 58 is programmed to clear the desired bits. This programming is done in a manner similar to that for programming the HLOCK bit including resetting user lock bit 59 after programming the corresponding character bits 57 if desired.

During programming, clock generator 36 outputs a PROGRAM EEPROM signal to memory 28. This signal enables current to memory 28 to allow it to be operated on. Clock generator 36 counts from the time PROGRAM ENABLE enables the clock generator 36 and for a predetermined period sufficient to shift data from data module 40 into the EEPROM of memory 28. Once the predetermined count has been reached, PROGRAM EEPROM is disabled so that no current is provided to the memory, further conserving power.

Program control 46 also reads mode bit 76 of status byte 50. If mode bit 76 is set for example, only half or 16 characters of data region 56 can be accessed either for programming or reading. Mode bit 76 causes program control 46 to output a MODE signal to address module 38 which disables address module 38 from addressing or latching data in the second half of memory 28. As a result, the transponder will act as if it has a memory half the size. This is beneficial where a study utilizing smaller transponders can be mimicked so that a single transponder can mimic the style of an old study or a new study utilizing the programmable implantable transponder of the invention.

Lastly, if the data in data region 56 is to be permanently maintained, then seal bits 62, 64 may be set by programming ones into them. This is accomplished by first programming SEAL 0, then programming SEAL 1 in a way as described above with programming the HLOCK bit. In this way a programmable lock bit is provided. It should be noted that two bits are used as the permanent seal by way of example, but the seal bit could be one bit, two bits, three bits or more.

TEMPERATURE MODE

Figure 9A:
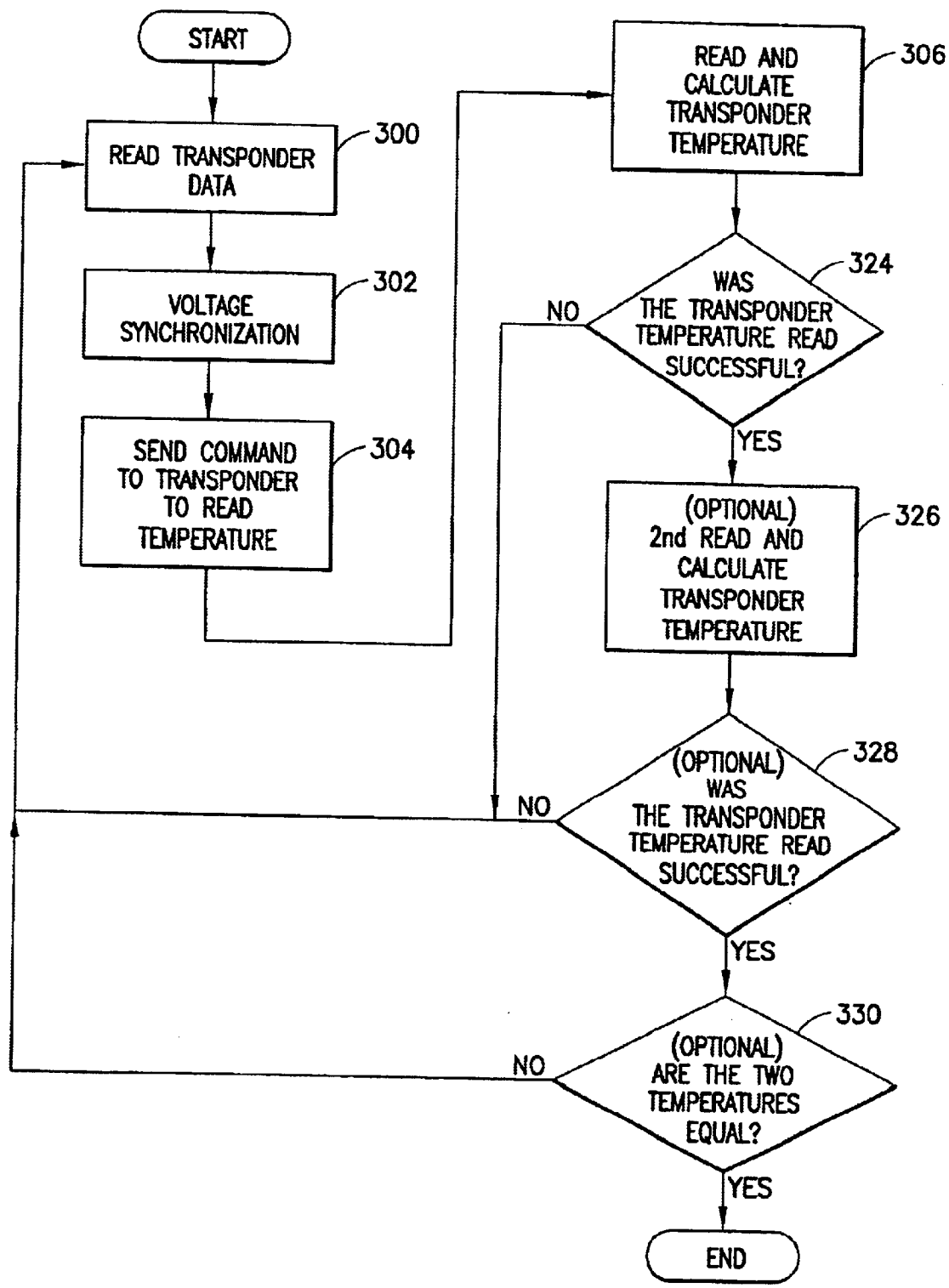
FIGS. 9(A), 9(B) are flow charts showing the method for measuring the temperature in accordance with the invention.
Figure 9B:
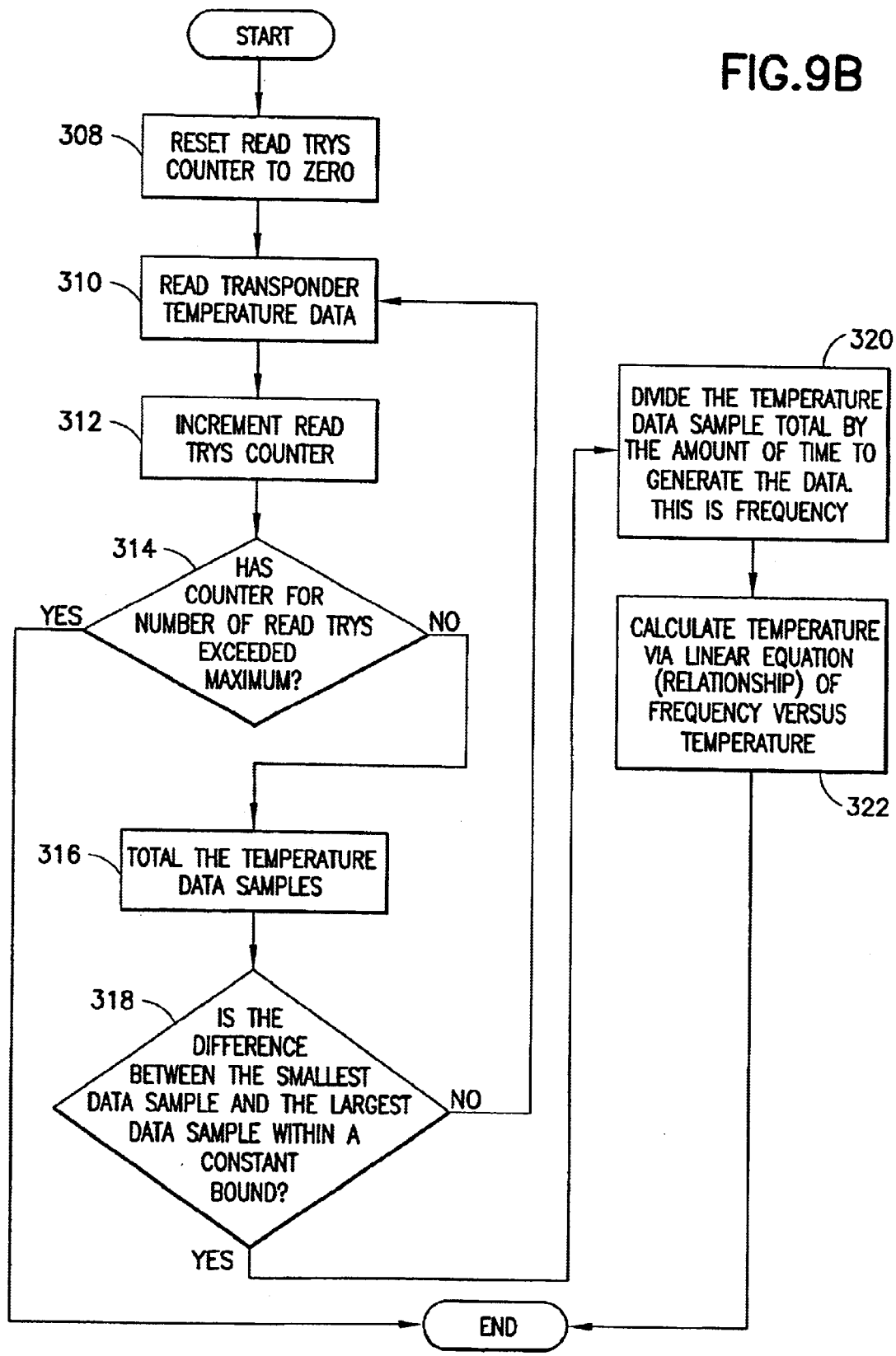
Figure 10:
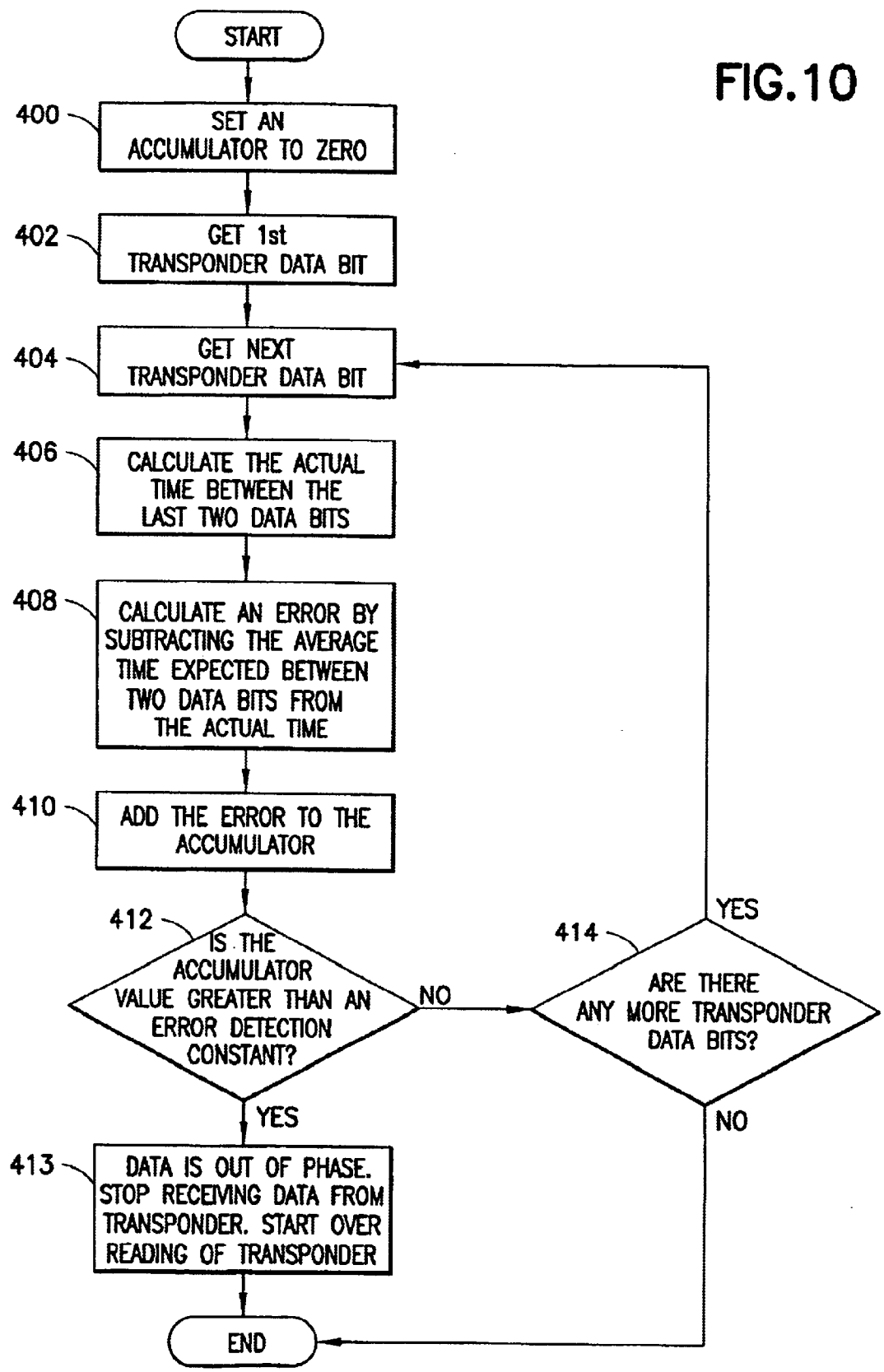
FIG. 10 is a flow chart showing the method for determining the integrity of the data read from the transponder.

During the TEMPERATURE MODE, the transponder is first read in a step 300 as shown in FIGS. 9(A), 9(B). In a step 302, voltage synchronization is performed to make sure that an appropriate voltage level temperature command will be sent and received. The voltage synchronization is that described above utilizing comparator 47. A temperature command is sent by interrogator 10 in a step 304 as a pulse space modulated signal as shown in FIG. 6. The signal may be of any length, but in the preferred embodiment, it is five bits and it is received by antenna 22 of transponder 20 and input to receiver 44.

A temperature module 30 is coupled to a thermistor 32. Thermistor 32 changes resistance as a function of temperature and outputs a frequency signal which changes with resistance. Temperature module 30 continuously counts the output of thermistor 32 and outputs the current count as a TEMP DATA signal to data module 40.

In step 306 receiver 44 receives the temperature command and outputs XMIT COMPLETE signal to address module 38 upon completion of the temperature command. The XMIT COMPLETE signal is also output to clock generator 36 and program control 46. Clock generator 36 outputs a LATCH TEMP signal to data module 40 on a periodic basis. At each occurrence of the LATCH TEMP signal, data module 40 outputs the current count of the TEMP DATA signal as a DATA OUT signal to transmitter 42. Transmitter 42 then outputs the latched count as the XMIT OUT signal to modulator 34 which modulates the signal and outputs the temperature count from antenna 22 to interrogator 10.

Because the frequency monitored by temperature module 30 varies with temperature, the count rate will vary with temperature. Clock generator 36, by outputting a consistent periodic LATCH TEMP signal at a predetermined interval, is utilized to standardize the sampling. This is done to reflect the changes in count as a function in temperature and not of time. In effect, each temperature sampling is the difference between successive latched counts.

Reference is made to FIG. 9B in which the steps 306 for reading transponder temperature data are provided in greater detail. CPU 12 of interrogator 10 has as part of its software a read tries counter. In step 308, the read tries counter is set to zero. In step 310, the temperature data is read as described above i.e. reading a plurality of latched samples. Interrogator 10 outputs a read command signal which results in interrogator 10 receiving a predetermined number of latched counts from temperature module 30. The read tries counter is incremented in a step 312. It is determined whether or not the counter for number of read tries exceeds a predetermined maximum in a step 314. If the number of tries has been exceeded, then this is an indicator that the temperature readings are inaccurate, and the temperature reading has been unsuccessful (step 324) because it is requiring too many tries to obtain an accurate reading and the process is begun again in a step 300 in which transponder data is read.

If the counter for the number of read tries has not exceeded the maximum, then the read has been successful and the temperature data samples are totaled in step 316. In step 318, as an integrity check, it is determined whether the difference between the count for the smallest data sample and the count for the largest data sample is within a predetermined range. If it falls outside of the range, then the variation is too great and the process is begun again at a step 310.

If the value is within the range, the total data sample temperature from step 316 is then divided by the amount of time required to generate all of the data in a step 320. This is the frequency output by the thermistor. Knowing the relationship between frequency and temperature for the given thermistor, the temperature is calculated in a step 322. In a step 324, it is determined whether the transponder read was successful. If not, the process is begun again at step 300. If the read was successful, then for verification a second read is taken in a step 326 by repeating steps 308–322. In a step 328 it is determined whether the second read was successful. If not, the process is restarted at step 300. If successful then the two counts are compared in a step 330. If they are equal, this temperature is displayed by interrogator 10. If they are not equal then the process is restarted at step 300.

INTEGRITY CHECK

In one embodiment of the invention, the interrogator performs an integrity check of the data being read from transponder 20. Because transponder 20 utilizes the interrogator signal from interrogator 10 as a master clock, interrogator 10 knows the length of time between bits of data transmitted to interrogator 10 by transponder 20. CPU 12 of interrogator 10 includes an accumulator. In a step 400, the accumulator is set to zero. In a step 402, the first transponder bit is received. In a step 404, the next transponder data bit is received. In a step 406 utilizing an on-board clock, interrogator 10 calculates the actual time elapsed between the last successive two data bits. In a step 408, the calculated time in a step 406 is subtracted from the average time expected between two bits. This number is an error number. In a step 410, the error number is added to the accumulator. In a step 412, it is determined whether the accumulator value is greater than an error detection constant. If the value is greater than an error detection constant, than this means the data is out of phase, and in a step 413 interrogator 10 stops receiving data from the transponder 20 and starts the read process over. If in step 412 the detection constant is still within acceptable tolerances, it is determined in a step 414 whether there are any more incoming transponder data bits. If there are more incoming bits, then the process is repeated at a step 404. If there are no more bits, then the received data is valid and the process is ended.

By utilizing the method, it is no longer required to wait until the very end of the read cycle to determine whether or not a bad read has occurred. Time is saved by arriving at an accurate read more quickly providing a benefit to the user.

It will thus be seen that the objects set forth above, among those made apparent from the preceding description, are efficiently attained and, since certain changes may be made in carrying out the above method in the construction(s) set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A transponder comprising:
a memory for storing data therein;
a clock generator for outputting a read signal for supplying current to the memory;
an address module for addressing a selected address from a plurality of addresses in the memory, said clock generator outputting an increase address signal and said address module selecting an address to be read in response to said increase address signal from said clock generator; and
a data module for receiving the data stored in said memory at said selected address indicated by said address module and for latching said data in response to a latch data signal from said clock generator, said clock generator stopping supplying said read signal to turn off said current to said memory each time the contents of a selected memory address from the plurality of addresses are output from the memory to the data module, said current thus being cycled on and off with each latching of the contents of each successive selected memory address in said data module.

2. The transponder of claim 1, wherein said clock generator outputs a program signal for supplying current to the memory to program the memory, and said address clock signal is an address latch signal, the address module selecting a specific address of the memory in response to the address latch signal, said data module inputting data to the memory at the address indicated by the address module, said clock generator stopping supplying current to the memory once the data in the data module has been stored in the memory.

3. The transponder of claim 1, further comprising a program control and said memory having a status byte region and a data region, said program control reading data from said status byte region and in response thereto, outputting a program enable signal to said clock generator to enable said clock generator to output said address signal to said address module.

4. The transponder of claim 3, wherein said status byte region stores at least a first seal bit and a second seal bit, said program control reading said first seal bit and said second seal bit and outputting the program enable signal if at least one of said first seal bit and second seal bit is clear.

5. The transponder of claim 3, wherein said status byte includes an HLOCK bit, said HLOCK bit being capable of being set or clear, said program control reading said HLOCK bit and receiving an address from said address module, and outputting said program enable if said HLOCK bit is clear or said HLOCK bit is set and said address output, by said address module corresponds to the address of the status byte within said memory.

6. The transponder of claim 5, wherein said status byte further includes a mode bit, said program control reading said mode bit and providing an output to said address module preventing said address module from accessing addresses in said memory not corresponding to the mode indicated by said mode bit.

7. The interrogator of claim 1, wherein the clock generator outputs an address latch signal to said address module in response to a program signal from an interrogator, said address latch signal causing said address module to select an address to be programmed in accordance with said program signal, said program signal being pulse space modulated.

8. The transponder of claim 1, the transponder further comprising:

a comparator for receiving said interrogator signal and a reference voltage and outputting a first logic level if the voltage of the interrogator signal is greater than the reference voltage, and outputting a second logic level if the voltage of the interrogator signal is less than the reference voltage; and a transmitter for receiving said first and second logic levels and outputting a first voltage indicator signal in response to said first logic level and outputting a second voltage indicator signal in response to said second voltage level, the first signal being the inverse of the second signal to indicate to an interrogator a received relative voltage level.

9. The transponder of claim 1, wherein said transponder is formed as an integrated circuit and further comprising a clamp, the clamp including at least one MOSFET.

10. The transponder of claim 9, wherein said clamp is formed by a CMOS process.

11. The transponder of claim 1, said transponder further comprising an integrated circuit, said integrated circuit including a clamp, the clamp including at least one MOSFET.

12. The transponder of claim 11, wherein said clamp is formed in a CMOS process.

13. A transponder comprising:

a memory for storing data therein, said memory having addresses;

a clock generator outputting a program signal for supplying current to the memory to program the memory;

an address module for addressing a selected address from a plurality of addresses in the memory, said clock generator outputting an address latched signal, said address module selecting selected address to be read in response to the address latch signal; and a data module for inputting data to the memory at the address indicated by the address module, said clock generator stopping supplying current to the memory each time the contents of a selected memory address from the plurality of addresses has been stored in the memory, said current thus being cycled on and off with each storing of the contents of each successive selected memory address of the plurality of memory addresses in the memory.

14. The transponder of claim 13, further comprising a program control and said memory having a status byte region and a data region, said program control reading data from said status byte region and in response thereto, outputting a program enable signal to said clock generator to enable said clock generator to output said address signal to said address module.

15. The transponder of claim 14, wherein said status byte region stores at least a first seal bit and a second seal bit, said program control reading said first seal bit and said second seal bit and outputting the program enable signal if at least one of said first seal bit and second seal bit is clear.

16. The transponder of claim 14, wherein said status byte includes an HLOCK bit, said HLOCK bit being capable of being set or clear, sad program control reading said HLOCK bit and receiving an address from said address module, and outputting said program enable if said HLOCK bit is clear or said HLOCK bit is set and said address output by said address module corresponds to the address of the status byte within said memory.

17. A transponder comprising:

a memory, said memory including a data region and a status byte region;

a clock generator for receiving a program signal and outputting a data latch signal in response thereto;

an address module for receiving said address latch signal and addressing a predetermined address from a plurality of addresses in the memory to be programmed; and a program control for reading said status byte and outputting a program enable signal in response thereto, said clock generator receiving said program enable signal and outputting said address latch in response to said program enable signal a data module for receiving the data stored in said memory at an address indicated by said address module, said clock generator stopping supplying said read signal to turn off said current to said memory each time the data from a predetermined address has been output to said data module, said current thus being cycled on and off with each outputting of the data of each successive address of the plurality of address.

18. The transponder of claim 17, wherein said status byte region stores at least a first seal bit and a second seal bit, said program control reading said first seal bit and said second seal bit and outputting the program enable signal if at least one of said first seal bit and second seal bit is not set.

19. The transponder of claim 17, wherein said status byte includes an HLOCK bit, said HLOCK bit being capable of being set or clear, said program control reading said HLOCK bit and receiving an address from said address module, and outputting said program enable if said HLOCK bit is clear or said HLOCK bit is set and said address output by said address module corresponds to the address of the status byte within said memory.

* * * * *